United States Patent [19]

Duffett

[11] Patent Number: Plant 5,475

[45] Date of Patent: May 21, 1985

[54] CHRYSANTHEMUM PLANT NAMED SILVERADO

[75] Inventor: William E. Duffett, Salinas, Calif.

[73] Assignee: Yoder Brothers, Inc., Barberton, Ohio

[21] Appl. No.: 526,085

[22] Filed: Aug. 24, 1983

[51] Int. Cl.[3] ..... A01H 5/00
[52] U.S. Cl. ..... Plt./74
[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Silverado particularly characterized as to uniqueness by the combined characteristics of flat capitulum form; daisy capitulum type; white ray floret color; diameter across face of capitulum ranging from 50 to 65 mm. at maturity; uniform ten week photoperiodic flowering response to short days; tall plant height when grown single stem; 10 to 15 cm. peduncles on open, normally terminal sprays, and slow development of male sterile green discs.

3 Drawing Figures

The present invention comprises a new and distinct cultivar of *Chrysanthemum morifolium,* Ramat., named Silverado.

Silverado is a product of a planned breeding program which had the objective of creating new chrysanthemum cultivars for cut spary mum programs with daisy capitulum type, white ray floret color, nine to ten week flowering response, and having the ability to produce commercially acceptable quality primarily in fall, winter and spring low light programs. Such traits in combination were not present or required improvement in previously available commercial cultivars.

Silverado was originated from a cross made in a controlled breeding program in Salinas, Calif. in 1977. The female parent was the unpatented cultivar identified as Blue Marble, a pink mutation of Pink Marble, originated by the present inventor. The male parent of Silverado was an unnamed seedling identified as 72118005, a white anemone originated from a cross between Pink Marble and Top Flight.

Silverado was discovered and selected as one flowering plant within the progeny of the stated cross by William E. Duffett on Nov. 25, 1978 in a controlled environment in Salinas, Calif.

The first act of asexual reproduction of Silverado was accomplished when vegetative cuttings were taken from the initial selection in February 1979 in a controlled environment in Salinas, Calif. by a technician working under formulations established and supervised by William E. Duffett.

Horticultural examination of selected units initiated March 1980 has demonstrated that the combination of characteristics as herein disclosed for Silverado are firmly fixed and are retained through successive generations of asexual reproduction.

Silverado has not been observed under all possible environmental conditions. The phenotype may vary significantly with variations in environment such as temperature, light intensity, and day length. The following observations, measurements and comparisons describe plants grown in Salinas, Calif. under greenhouse conditions which approximate those generally used in commercial practice.

The following traits have been repeatedly observed and are determined to be basic characteristics of Silverado which in combination distinguish this chrysanthemum as a new and distinct cultivar:

(1) Flat capitulum form.

(2) Daisy capitulum type.

(3) White ray floret color with minimum color oxidation.

(4) Green (immature) to yellow-green (mature) disc floret color.

(5) Diameter across face of capitulum ranging from 50 to 65 mm. at maturity.

(6) Uniform ten week photoperiodic flowering response to short days.

(7) Medium peduncle length, ranging from 10 to 15 cm.

(8) Tall plant height (requiring 1 to 2 long day weeks prior to short days to attain a flowered plant height of 80 to 90 cm. for year round flowering).

(9) Minimum temperature requirement of 16° C. (60° F.) for bud initiation when grown in single stem cut spray programs with a continuous dark period of 13 to 14 hours.

(10) Disc florets are pollen free, a condition known as male sterility.

The accompanying photographic drawings show typical inflorescence and foliage characteristics of Silverado, with the colors being as nearly true as possible with illustrations of this typ. Sheet 1 is a color photograph of Silverado grown as a single stem cut spray. Sheet 2 is a black and white photograph showing the top and underside of the leaves of Silverado at three stages of development (mature, intermediate, and immature). Sheet 3 is a black and white photograph of three views of the inflorescence of Silverado.

Of the many commercial cultivars known to the present inventor, the most similar in comparison to Silverado is White Marble. Reference is made to attached Chart A which compares certain characteristics of Silverado to those same characteristics of White Marble.

In comparison to White Marble, Silverado has the same ray floret color, with equal color retention; its spray formation is generally terminal; its crown cycle is longer and does not produce low crowns as does White Marble; it has a smaller diameter across the face of the capitulum by 10 to 15 mm., and taller plant height by approximately 15 cm.,; and it has a more rapid development of lateral inflorescenses down the stem. The flowering response to short days is 5 to 7 days later. The stems of Silverado are solid and firm. Those of White Marble are frequently hollow.

In the following description, color references are made to The Royal Horticultural Society Colour Chart. The color values were determined between 3:00 PM and 3:30 PM on Nov. 24, 1982 under 150 foot-candle light intensity at Salinas, Calif.

CLASSIFICATION

Botanical: *Chrysanthemum morifolium,* Ramat., cv SILVERADO.

Commercial: Cut daisy spray.

INFLORESCENCE

Capitulum:

*Form.*—Flat.

*Type.*—Daisy.

*Diameter across face.*—50 To 65 mm.

Corolla of ray florets:

*Color (general tonality from a distance of three meters).*—White.

*Color (abaxial).*155D.

*Color (adaxial).*155B.

*Shape.*—Short, broad, rounded tip.

Corolla of disc florets

*Color (mature).*153C.

*Color (immature).*154A.

Reproductive organs:

*Androecium.*—Disc florets present with no pollen, a male sterile condition.

*Gynoecium.*—Present both ray and disc florets.

PLANT

General appearance:

*Height.*—Tall, 70 to 80 cm., as a flowering plant from a rooted cutting, with no long days for May through October flowerings and maintaining a minimum nightly 13 hour continuous dark period.

FOLIAGE

*Color (abaxial).*147A.

*Color (adaxial).*147B.

*Shape.*—Deeply lobed and moderately serrated.

CHART A

COMPARISON OF SILVERADO AND WHITE MARBLE

| CULTIVAR | RAY FLORET COLOR | CAPITULUM FORM AND TYPE |
|---|---|---|
| SILVERADO | WHITE DEVOID OF PINK TINGING | FLAT DAISY |
| WHITE MARBLE | WHITE DEVOID OF PINK TINGING | FLAT DAISY |

| SPRAY FORMATION | DIAMETER ACROSS FACE OF CAPITULUM | PLANT HEIGHT | FLOWERING RESPONSE PERIOD |
|---|---|---|---|
| TERMINAL 10 to 15 cm PEDUNCLES | 50 to 65 mm. | TALL | 10 WEEK |
| FREQUENTLY COMPOUND 15 to 20 cm PEDUNCLES | 60 to 70 mm. | MEDIUM | 9 WEEK |

COMPARISONS MADE OF PLANTS GROWN AS SINGLE STEM CUT SPRAYS WITH NO LONG DAYS IN SALINAS, CALIFORNIA

I claim:

1. A new and distinct plant of *Chrysanthemum morifolium,* Ramat., named Silverado, as described and illustrated, and particularly characterized as to uniqueness by the combined characteristics of flat capitulum form; daisy capitulum type; white ray floret color; diameter across face of capitulum ranging from 50 to 65 mm. at maturity; uniform ten week flowering response; tall plant height when grown single stem; 10 to 15 cm. peduncles on open, normally terminal sprays, and slow development of male sterile green discs.

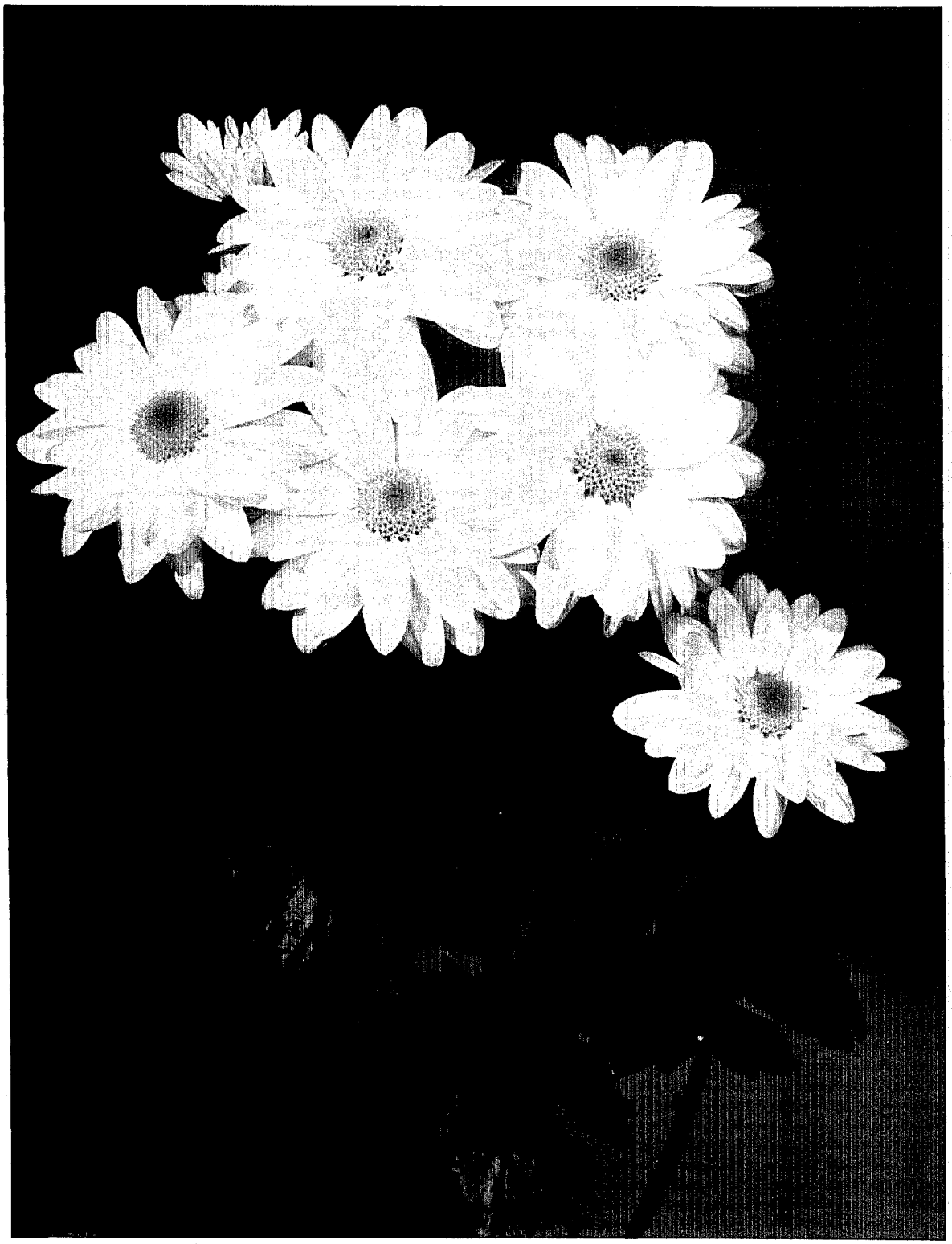

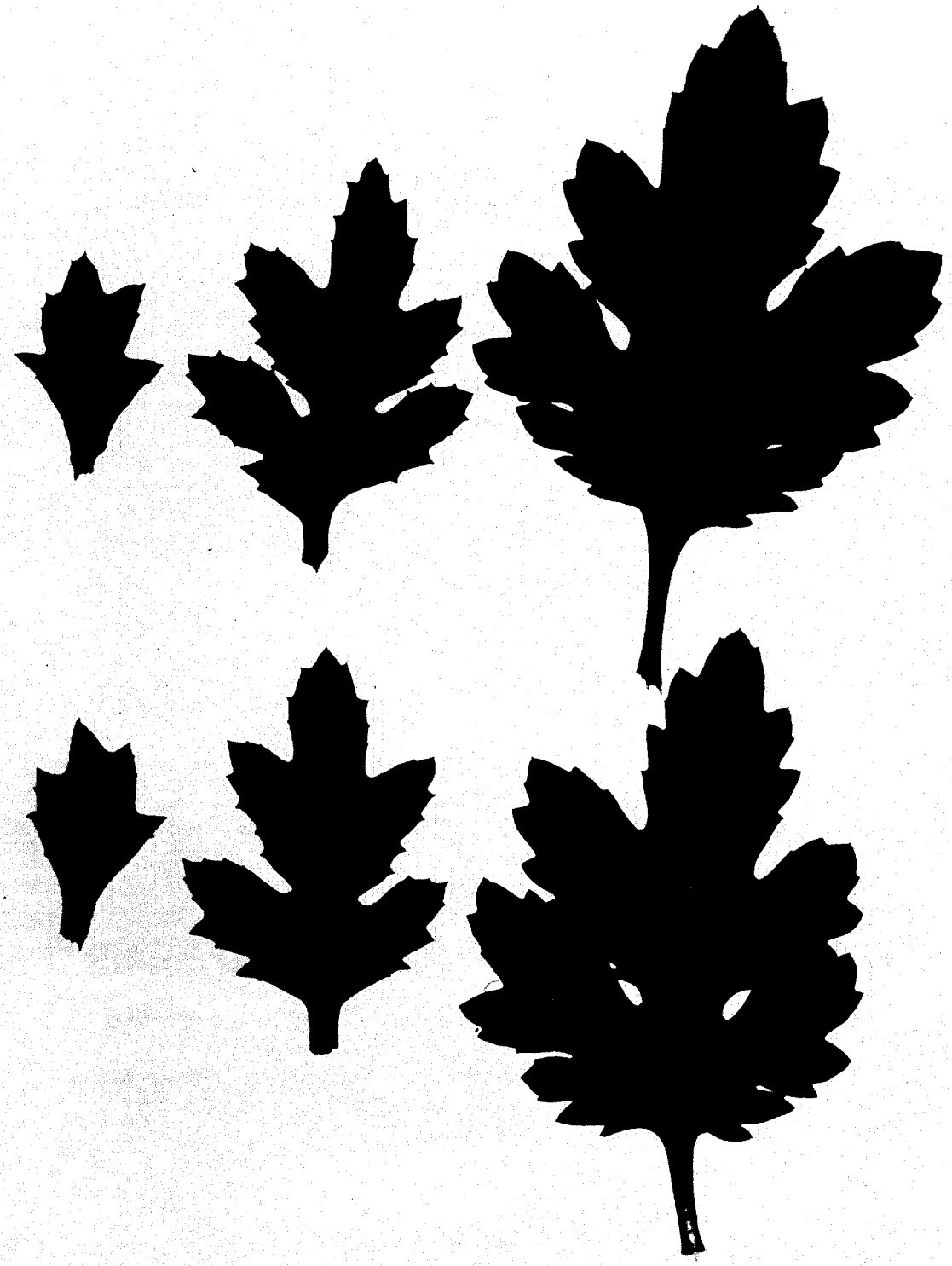

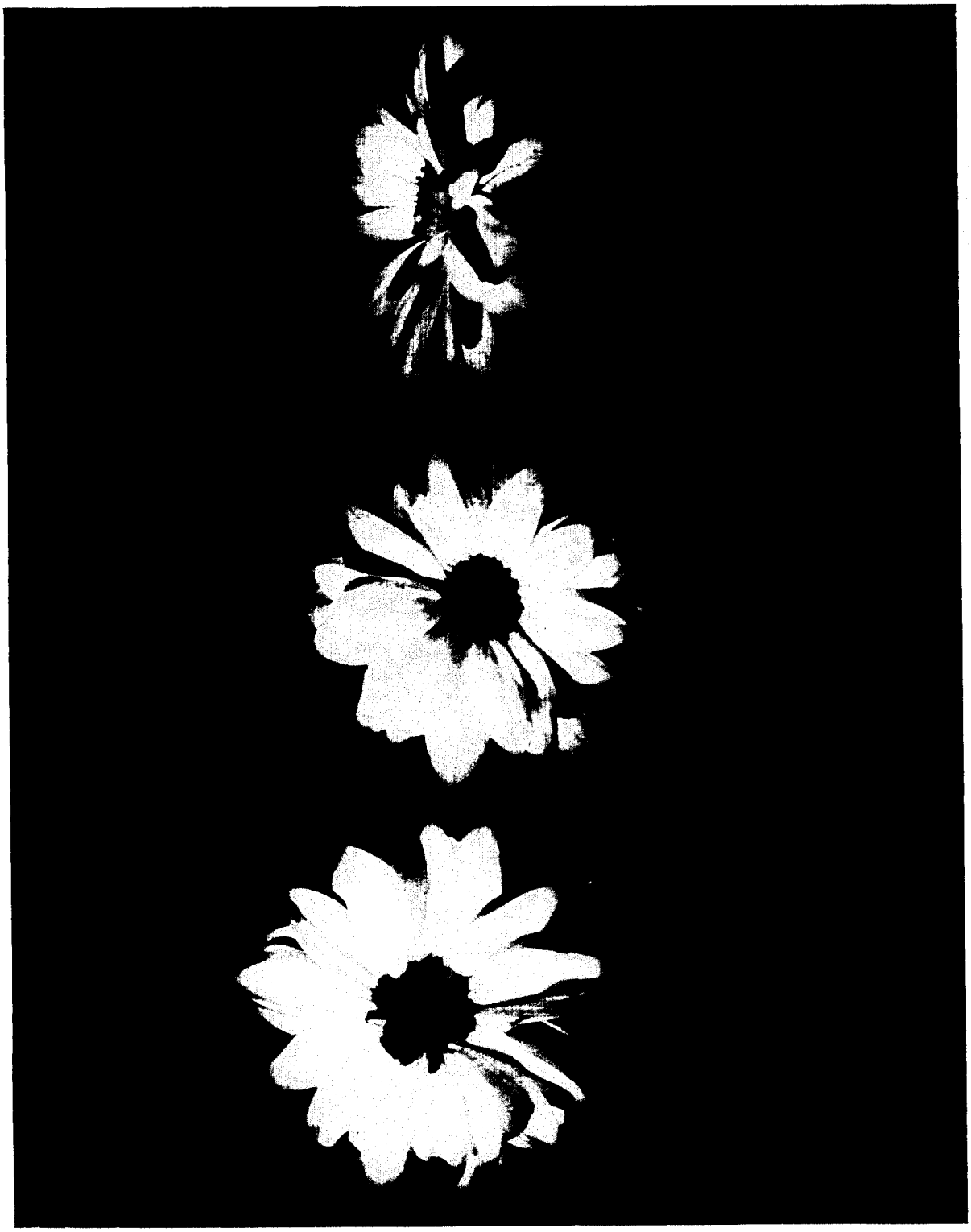

* * * * *